US006372283B1

(12) United States Patent
Shim et al.

(10) Patent No.: US 6,372,283 B1
(45) Date of Patent: Apr. 16, 2002

(54) PLASMA PROCESS FOR SURFACE MODIFICATION OF PYROLITIC CARBON

(75) Inventors: Hong S. Shim, Santa Ana; Mark C. S. Shu, Mission Viego, both of CA (US); David L. Miller, Circle Pines, MN (US); Edward Di Domenico, Anoka, MN (US); Catherine E. Taylor, Minneapolis, MN (US); Kenneth Keeney, Forest Lake, MN (US); Mark T. Stewart, Lino Lakes, MN (US); Eileen L. Halverson, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/285,953

(22) Filed: Apr. 2, 1999

(51) Int. Cl.$^7$ .............................. B05D 3/06; B05D 7/02; A61F 2/24; A61L 27/34; A61L 27/44
(52) U.S. Cl. ...................... 427/2.25; 427/579; 427/489; 427/407.1; 427/2.24; 623/1.26
(58) Field of Search ................................ 427/489, 578, 427/579, 563, 407.1, 2.13, 2.25, 2.24; 623/1.26

(56) References Cited

U.S. PATENT DOCUMENTS

| | | | | |
|---|---|---|---|---|
| 4,267,211 A | * | 5/1981 | Yajima et al. ............... | 427/228 |
| 4,473,423 A | | 9/1984 | Kolff | |
| 4,510,628 A | | 4/1985 | Kolff | |
| 4,608,051 A | * | 8/1986 | Reck et al. .................... | 623/10 |
| 5,133,845 A | | 7/1992 | Vallana et al. | |
| 5,260,093 A | * | 11/1993 | Kamel et al. ............... | 427/489 |
| 5,370,684 A | | 12/1994 | Vallana et al. | |
| 5,387,247 A | | 2/1995 | Vallana et al. | |
| 5,439,736 A | * | 8/1995 | Nomura ....................... | 427/489 |
| 5,447,724 A | | 9/1995 | Helmus et al. | |
| 5,463,010 A | * | 10/1995 | Hu et al. .................... | 427/489 |
| 5,569,463 A | | 10/1996 | Helmus et al. | |
| 5,599,624 A | * | 2/1997 | Prochazka .................. | 428/375 |
| 5,607,580 A | * | 3/1997 | Betz et al. ................ | 210/198.2 |
| 5,723,172 A | * | 3/1998 | Sherman ...................... | 427/109 |
| 5,948,484 A | * | 9/1999 | Gudimenko et al. ......... | 427/489 |
| 6,013,855 A | * | 1/2000 | McPherson et al. ........ | 427/2.25 |
| 6,022,602 A | * | 2/2000 | Nomura ....................... | 427/489 |
| 6,139,575 A | * | 10/2000 | Shu et al. ................... | 623/2.12 |

OTHER PUBLICATIONS

Arkles, "Tailoring surfaces with silanes", *Chemtech*, 7:766–767 (1977). No month.
*Grant & Hackh's Chemical Dictionary*, 5th ed., New York, McGraw–Hill Book Co., p. 256 (1987). No month.
*Polymer Technology Dictionary*, 1st ed., London, Chapman & Hall, p. 335 (1994). No month.
Triolo et al., "Surface Modification and Characterization of Some Commonly Used Catheter Materials. II. Friction Characterization", *Journal of Biomedical Materials Research*, 17:149–165 (1983). no month.
Allmer et al., "Surface Modification of Polymers. V. Biomaterial Applications", *J. of Polymer Science*, vol. 28:173–183 (1990). no month.
"Applying a Silane Coupling Agent", Brochure from Gelest Inc., pp. 88–89 no date.

(List continued on next page.)

Primary Examiner—Marianne Padgett
(74) Attorney, Agent, or Firm—Thomas G. Berry; Daniel W. Latham (57) ABSTRACT

The present invention provides a method for modifying a pyrolytic carbon surface to improve adhesion between it and a subsequently added polymer and/or a bio-active compound. In particular, plasma depositing an oxygen-containing, silicon-containing film forming monomer on a pyrolytic carbon surface improves adhesion of a polymer thereto, wherein the modified pyrolytic carbon surface and silicone rubber has a wet adhesion peel force greater than the wet adhesion peel force between an unmodified pyrolytic carbon and silicone rubber as measured by ASTM D 903-49 after 28 days in an aqueous environment, typically, at least 10 times greater.

22 Claims, 3 Drawing Sheets

OTHER PUBLICATIONS

Arkles, "Tailoring surfaces with silanes", *Chemtech*, vol. 7, 766–767 (1977). no month.

Bergbreiter, "Polymer Surface Derivatizatoin", Texas A&M University, College Station, Texas, MSE–ACS Workshop of Polymer Surface Science No date.

Goodman et al., "Three–dimensional Morphology and Platelet Adhesion on Pyrolytic Carbon Heart Valve Materials," *Cells and Materials*, vol. 5, No. 1, pp. 15–30 (Scanning Electron Microscopy International, 1995). no month.

Gombatz and Hoffmann, editors "Gas–Discharge Techniques For Biomaterial Modifications" *CRC Critical Reviews in Biocompatibility*, vol. 4, Issue 1 (1987) pp 1–42. no month Ikada, "Surface Modification of Polymers for Medical Applications," *Biomaterials*, vol. 15:725–736 (1994). No month.

King et al., "Surface Analysis of Silicon: Alloyed and Unalloyed LTI Pyrolytic Carbon," *Photon. Electron. and Ion Probes*, ACS Symposium Series 162, D. Dwright et al, eds., Washington, D.C. (1981).p. 383–403 Mar. 25–27, 1980.

Kulik, et al., "Peroxide Generation and Decomposition on Polymer Surface," *J. of Polymer Science: Part A: Polymer Chemistry*, vol. 33:323–330 (1995).no month.

LaGrange et al., "Compatibility of Carbon and Blood," *National Heart Institute, Artificial Heart Program*, Artificial Heart Program Conference Proceedings, Chapter 5, (1969). Jun. 9–13, 1969.

McPherson et al., "Covalent Grafting of PEO to Inorganic Surfaces," *J. Biomedical Materials*, vol. 38:289–302 (1997). no month.

Ruckert et al., "Surface Modification of Polymers—IV. Grafting of Acrylamide via an Unexpected Mechanism Using a Water Soluble Photo–Initiator", *Eur. Polym. J.*, vol. 32, 201–208 (1996). no month.

Sheu et al., "A glow discharge treatment to immobilize poly(ethylene oxide)/poly(propylene oxide) surfactants for wettable and non–fouling biomaterials", *Contact Angle, Wettability and Adhesion*, pp. 531–545, (ed. K.L Muttal), VSP (1993). No month.

Triolo and Andrade, "Surface Modification and Evaluation of Some Commonly Used Catheter Materials I Surface Properties", *Journal of Biomedical Materials Research*, vol. 17, 127–147 (1983). no month.

Tunca, "Aqueous Polymerization of Methyl Methacrylate Initiated by Redox Pair: Ce (IV)—Azo Compounds with Methylol Functional Groups and Synthesis of Copolymers", *Jounral of Applied Polymer Science*, vol. 54, 1491–1497 (1994). no month.

Yuan et al., "Immobilization of Heparin Oligosaccharides onto Radiofrequency Plasma Modified Pyrolytic Carbon–Coated Graphite", *Journal of Applied Biomaterials*, vol. 6, 259–266 (1995). no month.

* cited by examiner

PLASMA PROCESS FOR SURFACE MODIFICATION OF PYROLITIC CARBON

FIELD OF THE INVENTION

The present invention relates to surface modifications of pyrolytic carbon and to a method for effecting such modifications.

BACKGROUND OF THE INVENTION

Pyrolytic carbon is one material of choice for use in vivo devices where relatively long term exposure to blood can be expected, such as prosthetic heart valves, the morphology of which has been reported by Goodman et al., "Three-dimensional Morphology and Platelet Adhesion on Pyrolitic Carbon Heart Valve Materials," *Cells and Materials*, Vol. 5, No. 1, pp. 15–30 (Scanning Electron Microscopy International, 1995). Pyrolytic carbon is not only effective in increasing the strength of the in vivo device but it also exhibits improved wear-resistant characteristics and deterioration even when implanted within the body for long periods of time.

In some biomedical applications, a more wear-resistance surface is required. One way of modifying pyrolytic carbon for such uses includes alloying the pyrolytic carbon with a silicon carbide base, which is described by King et al., "Surface Analysis of Silicon: Alloyed and Unalloyed LTI Pyrolytic Carbon," *Photon, Electron, and Ion Probes*, ACS Symposium Series 162, Washington, D.C. (1981). Additionally, it may be desirable to modify a carbon surface to enhance biocompatibility. LaGrange et al. described methods for attaching heparin with and without benzalkonium chloride on a porous carbon surface. LaGrange et al., "Compatibility of Carbon and Blood," *National Heart Institute, Artificial Heart Program*, Artificial Heart Program Conference Proceedings, Chapter 5, (1969). McPherson et al. describes an alternate method for reducing thrombogenicity of an inorganic surface, such as glass, nitinol, and pyrolytic carbon primed with trichlorovinylsilane by grafting poly(ethylene oxide) or a poly(ethylene oxide) surfactant on the inorganic surface using gamma radiation. McPherson et al., "Covalent Grafting of PEO to Inorganic Surfaces," *J. Biomedical Materials*, Vol. 38:289–302 (1997).

SUMMARY OF THE INVENTION

What is yet needed is a method for surface modifying a pyrolytic carbon surface, for example in an in vivo device, in such a way so as to be useful in promoting adhesion when attaching a polymer to the surface of an implantable device.

One aspect of the present invention provides a method for modifying a pyrolytic carbon surface including providing a substrate having at least one pyrolytic carbon surface to a reaction chamber; depositing an oxygen-containing, silicon-containing film forming monomer on the at least one pyrolytic carbon surface; and priming the at least one pyrolytic carbon surface having the oxygen-containing, silicon-containing film forming monomer deposited thereon with a organosilane compound.

As used herein, "silane" and "organosilane" refer to a saturated linear branched or unbranched compound having the nonhydrolyzed formula $R_nSiM_{4-n}$, wherein n is preferably greater than 1. Preferably, M is selected from the group consisting of a halogen, a alkoxy group, an acyloxy group, or an amine group. R is preferably a hydrocarbon group that is classified as an aliphatic group, cyclic group, or a combination of aliphatic and cyclic groups (e.g., alkaryl and aralkyl groups). In the context of the present invention, the term "aliphatic group" means a saturated or unsaturated linear or branched hydrocarbon group. This term is used to encompass alkyl, alkenyl, and alkynyl groups, for example. The term "alkyl group" means a saturated linear or branched hydrocarbon group, including, for example, methyl, ethyl, isopropyl, t-butyl, heptyl, dodecyl, octadecyl, amyl, 2-ethylhexyl, and the like. The term "alkenyl group" means an unsaturated linear or branched hydrocarbon group with one or more carbon-carbon double bonds, such as a vinyl group. The term "alkynyl group" means an unsaturated linear or branched hydrocarbon group with one or more triple bonds. The term "cyclic group" means a closed ring hydrocarbon group that is classified as an alicyclic group, aromatic group, or heterocyclic group. The term "alicyclic group" means a cyclic hydrocarbon group having properties resembling those of aliphatic groups. The term "aromatic group" or "aryl group" means a mono- or polynuclear aromatic hydrocarbon group. The term "heterocyclic group" means a closed ring hydrocarbon in which one or more of the atoms in the ring is an element other than carbon (e.g., nitrogen, oxygen, sulfur, etc.).

The term "group" is used to describe a chemical substituent that includes the unsubstituted group and the group with nonperoxidic O, N, or S atoms, for example, in the chain as well as carbonyl groups or other conventional substitution. For example, the phrase "alkyl group" is intended to include not only pure open chain saturated hydrocarbon alkyl substituents, such as methyl, ethyl, propyl, t-butyl, and the like, but also alkyl substituents bearing further substituents known in the art, such as hydroxy, alkoxy, alkylsulfonyl, halogen atoms, cyano, nitro, amino, carboxyl, etc. Thus, "alkyl group" includes ether groups, haloalkyls, nitroalkyls, carboxylalkyls, hydroxylalkyls, sulfoalkyls, etc. Preferably, the oxygen-containing, silicon-containing film forming monomer comprises a siloxane, preferably an organosiloxane.

As used herein, "siloxane" and "organosiloxane" refer to a linear or cyclic oxygen-containing, silicon-containing compound having the general formula $(Si-O-Si)_zR'_{3x}$, wherein R' is a hydrocarbon group that is preferably an aliphatic group, further wherein z is 1 or more and x is 1 or more. When x is more than 1, R' can each be the same or a different hydrocarbon group. In the context of the present invention, the term "aliphatic group" means a saturated or unsaturated linear or branched hydrocarbon group. This term is used to encompass alkyl, alkenyl, and alkynyl groups, for example. The term "alkyl group" means a saturated linear or branched hydrocarbon group, including, for example, methyl, ethyl, isopropyl, t-butyl, heptyl, dodecyl, octadecyl, amyl, 2-ethylhexyl, and the like. The term "alkenyl group" means an unsaturated linear or branched hydrocarbon group with one or more carbon-carbon double bonds, such as a vinyl group. The term "alkynyl group" means an unsaturated linear or branched hydrocarbon group with one or more triple bonds. Preferably, R' has the general formula $(C_yH_{2y+1})$.

A method in accordance with the present invention may further include the step of adding a polymer to the at least one pyrolytic carbon surface primed with the silane compound. Preferably, the polymer is selected from the group consisting of a natural hydrogel, a synthetic hydrogel, teflon, silicone, polyurethane, polysulfone, cellulose, polyethylene, polypropylene, polyamide, polyimide, polyester, polytetrafluoroethylene, polyvinyl chloride, epoxy, phenolic, neoprene, polyisoprene, and a combination thereof.

A method in accordance with the present invention may also include a step of adding a bio-active compound to the at least one pyrolytic carbon surface primed with the silane compound. Preferably, the bio-active compound is selected from the group consisting of an antithrombotic agent, an antiplatelet agent, an antimitotic agent, an antioxidant, an antimetabolite agent, an anti-inflammatory agent, and a combination thereof.

The step of depositing an oxygen-containing, silicon-containing film forming monomer on the at least one pyrolytic carbon surface preferably includes plasma depositing the film forming monomer in the presence of an inert gas. Typically, the inert gas is selected from the group of argon, helium, nitrogen, neon, and a combination thereof. If an inert gas is included, the film forming monomer is preferably in a ratio with the inert gas of about 20 parts film forming monomer to about 1 part inert gas.

In a method in accordance with the present invention, plasma depositing the film forming monomer occurs for a time period from about 10 minutes or less, preferably about 15 seconds to about 4 minutes.

Another aspect of the present invention provides a method of increasing adhesion between a pyrolytic carbon surface and a polymer. The method includes the steps of providing a substrate having at least one pyrolytic carbon surface to a reaction chamber; depositing an oxygen-containing, silicon-containing film forming monomer on the at least one pyrolytic carbon surface; priming the at least one pyrolytic carbon surface having the oxygen-containing, silicon-containing film forming monomer deposited thereon with a silane compound; and adding a polymer to the at least one pyrolytic carbon surface primed with the silane compound.

A further aspect of the present invention provides a method for attaching a polymer to a prosthetic heart valve comprising at least one pyrolytic carbon surface. The method includes the steps of forming a film on the at least one pyrolytic carbon surface of the heart valve, wherein the film is formed from an oxygen-containing, silicon-containing film forming monomer; priming the at least one pyrolytic carbon surface having the oxygen-containing, silicon-containing film forming monomer film thereon with a silane compound; and adding silicone to the at least one pyrolytic carbon surface primed with the silane compound.

Also provided is a modified pyrolytic carbon surface exhibiting increased adhesion to a polymer produced by a method in accordance with the present invention, wherein a wet adhesion peel force of the modified pyrolytic carbon surface and the polymer is at least 10 times greater than the wet adhesion peel force between an unmodified pyrolytic carbon and silicone rubber as measured by ASTM D 903-49 after 28 days in an aqueous environment.

DETAILED DESCRIPTION OF THE PREFERRED EMBODIMENTS

The present invention provides a method for modifying a pyrolytic carbon surface to enhance adhesion of a polymer to a pyrolytic carbon surface. Improved polymer adhesion is particularly important for implantable devices which undergo repeated stresses and/or are in long term contact with whole blood, such as prosthetic heart valves, orthopedic prostheses, pacemaker leads, stents, and the like. Such polymers can be utilized to modify the physical characteristics, such as sound dampening, to modify the physiological characteristics, such as anti-thrombogenecity, of an implantable device, or a combination thereof. Improved polymer adhesion to a pyrolytic carbon surface has been shown by dry and wet average peel force using a 180° peel test per ASTM D 90349.

While specific reference herein maybe made to prosthetic heart valves, it is to be understood that surface modification to other implantable and/or prosthetic devices is also encompassed by the present invention. For example, other devices can include leads, stents, orthopedic prostheses, all of which may have implications in the human body as well as in veterinary applications, such as internal skeletal structure for joint and/or bone replacement.

Surface modification of pyrolytic carbon preferably includes plasma deposition of a reactant monomer. Plasma reactors are known in the art, examples of which are described by Yasuda, H., *Plasma Polymerization*, Academic Press (Orlando, Fla., 1985); and d'Agostino, R., *Plasma Deposition, Treatment, and Etching of Polymers*, Academic Press (San Diego, Calif., 1990). Typically, such plasma reactors use wave energy (RF or microwave) to excite plasma.

In general, a plasma reactor for use in the present invention can include a glass reaction chamber which is fitted with a vacuum exhaust, gas inlets and at least one capacitively coupled electrode. In addition, the reactor is fitted with a pressure transducer and a mass flow controller for controlling and measuring the amount of gas being introduced into the reactor. The theory and practice of radio frequency (RF) gas discharge is explained in detail in 1) "Gas-Discharge Techniques For Biomaterial Modifications" by Gombatz and Hoffman, *CRC Critical Reviews in Biocompatibility*, Vol. 4, Issue 1 (1987) pp 1–42; 2) "Surface Modification and Evaluation of Some Commonly Used Catheter Materials I Surface Properties" by Triolo and Andrade, *Journal of Biomedical Materials Research*, Vol. 17, 129–147 (1983), and 3) "Surface Modification and Evaluation of Some Commonly Used Catheter Materials, II. Friction Characterized" also by Triolo and Andrade, *Journal of Biomedical Materials Research*, Vol. 17, 149–165 (1983).

Figure 1:
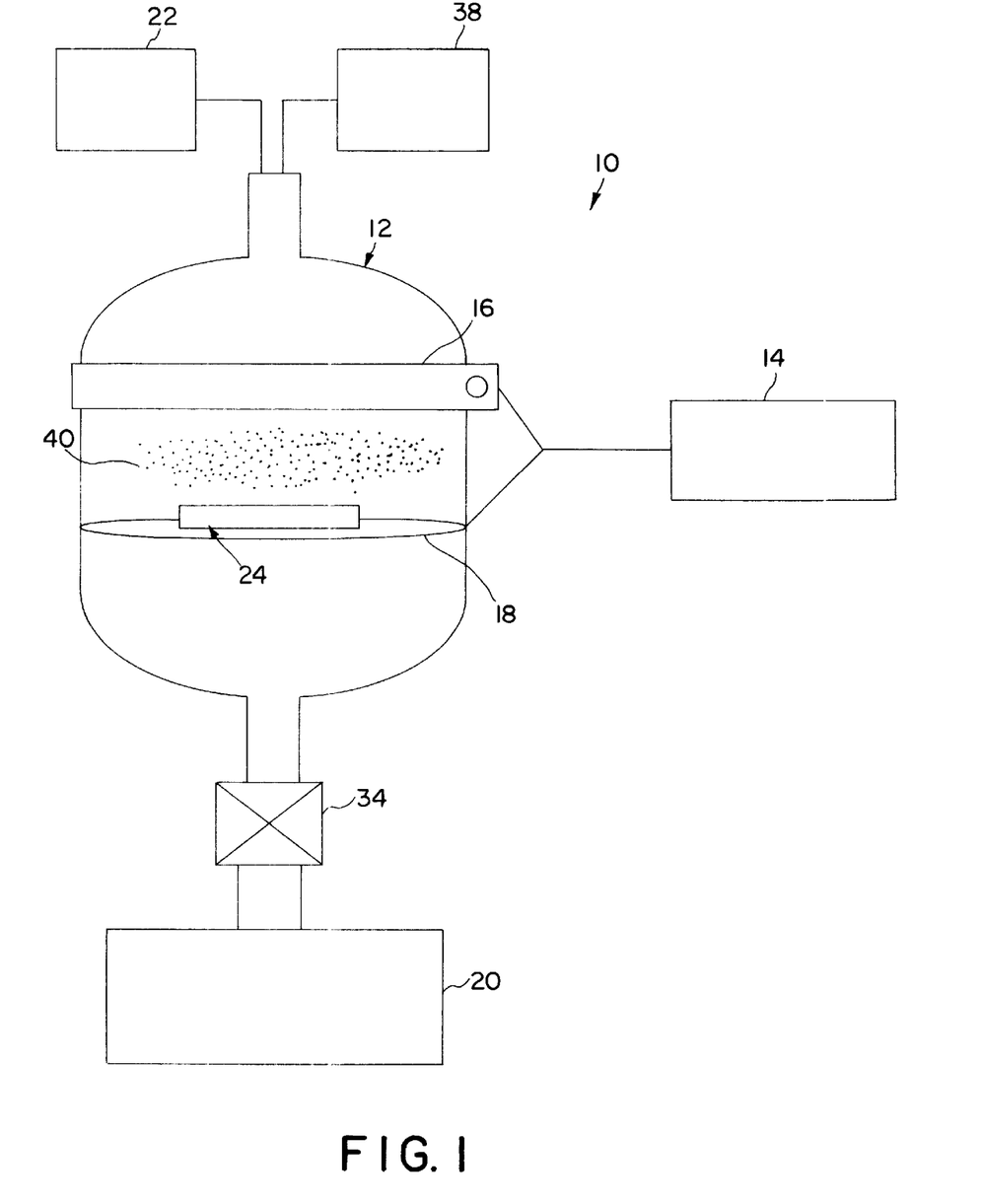
FIG. 1 is a schematic of an apparatus for use in a surface treatment method in accordance with the present invention.

FIG. 1 illustrates in schematic form a plasma reactor 10 that can be employed in a method in accordance with the present invention. The plasma at reactor 10 includes, in general, a vertical reaction chamber 12, R.F. power source 14 coupled across upper and lower electrodes 16 and 18, vacuum pump 20 and a reactant monomer source 22 in fluid communication with the reaction chamber 12. Preferably, the reactant monomer source 22 also includes a means for controlling the flow rate of the monomer (not shown).

A substrate having at least one pyrolytic carbon surface 24 is disposed on one electrode, for example, the lower electrode 18. Optionally, the electrode 18 can be brought to a suitable temperature by a heating/cooling unit (not shown) that is may be located in close proximity to electrode 18 and electrically controlled by a temperature control unit (not shown).

Optionally, a bellows (not shown) may be provided to adjust the spacing between the electrodes and, hence, controlling the confinement of the plasma 40. Preferably, a throttle valve 34 may be provided to control the pressure in the reaction chamber 12. The parameters that typically control the film characteristics formed from the reactant monomer include gas composition, gas flow rate, R.F. power, pressure, and temperature. Typically, the R.F. power can range from about 40 Watts to about 100 Watts, but is preferably at about 100 Watts. The pressure is typically about 0.1 Torr. Preferably, the deposition is allowed to continue from about 15 seconds to about 4 min., more preferably about 15 seconds.

Preferably, the reactant monomer is an oxygen-containing, silicon-containing film forming monomer. More preferably, the reactant monomer is a siloxane compound having the general formula $(Si-O-Si)_z R'_{3x}$, wherein z is 1 or more and x is 1 or more, and even more preferably, z is 1 and x is 1. Suitable reactant monomers include hexamethyldisiloxane (HMDS), polydimethylsiloxane, cyclic dimethylsiloxane, and the like. Typically, the reactant monomer is supplied at a gas flow of about 10.0 sccm.

Even more preferably, the reactant monomer is introduced into the reaction chamber with an inert gas from source 38 that may be in fluid communication with the reaction chamber 12. An inert gas can be selected from the group of argon, helium, nitrogen, neon, and the like. Combinations of the inert gases can also be beneficial to make the initiation of discharge easier. For example, argon can be added to neon in a minor amount to improve plasma initiation. Preferably, the monomer is provided in the reaction chamber in a ratio with the inert gas of about 20 parts monomer to about 1 part inert gas. For example, the monomer gas flow rate is more preferably about 10.0 sccm and the inert gas flow rate is more preferably typically about 0.5 sccm. Of course, one skilled in the art will readily appreciate that the deposition rate of the reactant monomer depends on the gas composition and is directly proportional to the gas flow rate, power, pressure, and is inversely proportional to temperature so that one could empirically determine the optimum parameters, such as those indicated above, for desired film characteristics.

Preferably, prior to plasma depositing an oxygen-containing, silicon-containing monomer on the pyrolytic carbon surface, it is thoroughly cleaned to remove any contaminating debris and the like. Conventional techniques can be used to adequately clean the surface, such as ultrasonic cleaning in an aqueous solution, solvent cleaning, and the like.

Once a pyrolytic carbon surface has been plasma modified as described above, a polymer can now be applied to the surface. In one embodiment of the present invention, a polymer useful in modifying the physical characteristics can now be applied by conventional methods.

Preferably, prior to applying a polymer to the plasma modified surface, the surface is primed in with a silane compound, preferably an organosilane compound, using conventional techniques. For example, the silane coupling agent can be dissolved at a %0% concentration in alcohol. One to three molar equivalents of water can be added to the silane/alcohol mixture and allowed to equilibrate. Optionally, this aqueous mixture can be diluted to a 10% concentration silane with a higher boiling point solvent. This silane composition can be applied to a surface by dipping, spraying, or other application techniques. The surfaces are then allowed to stand at ambient temperature for about 24 hours or can be placed at 110–120° C. for about 5–10 minutes.

Preferably, the silane coupling agent has the nonhydrolyzed formula $R_n SiM_{4-n}$, wherein n is preferably greater than 1. Preferably, M is selected from the group consisting of a halogen, a alkoxy group, an acyloxy group, or an amine group. R is preferably a hydrocarbon group that is classified as an aliphatic group, cyclic group, or a combination of aliphatic and cyclic groups (e.g., alkaryl and aralkyl groups). In the context of the present invention, the term "aliphatic group" means a saturated or unsaturated linear or branched hydrocarbon group. This term is used to encompass alkyl, alkenyl, and alkynyl groups, for example. The term "alkyl group" means a saturated linear or branched hydrocarbon group, including, for example, methyl, ethyl, isopropyl, t-butyl, heptyl, dodecyl, octadecyl, amyl, 2-ethylhexyl, and the like. The term "alkenyl group" means an unsaturated linear or branched hydrocarbon group with one or more carbon-carbon double bonds, such as a vinyl group. The term "alkynyl group" means an unsaturated linear or branched hydrocarbon group with one or more triple bonds. The term "cyclic group" means a closed ring hydrocarbon group that is classified as an alicyclic group, aromatic group, or heterocyclic group. The term "alicyclic group" means a cyclic hydrocarbon group having properties resembling those of aliphatic groups. The term "aromatic group" or "aryl group" means a mono- or polynuclear aromatic hydrocarbon group. The term "heterocyclic group" means a closed ring hydrocarbon in which one or more of the atoms in the ring is an element other than carbon (e.g., nitrogen, oxygen, sulfur, etc.).

The term "group" is used to describe a chemical substituent that includes the unsubstituted group and the group with nonperoxidic O, N, or S atoms, for example, in the chain as well as carbonyl groups or other conventional substitution. For example, the phrase "alkyl group" is intended to include not only pure open chain saturated hydrocarbon alkyl substituents, such as methyl, ethyl, propyl, t-butyl, and the like, but also alkyl substituents bearing further substituents known in the art, such as hydroxy, alkoxy, alkylsulfonyl, halogen atoms, cyano, nitro, amino, carboxyl, etc. Thus, "alkyl group" includes ether groups, haloalkyls, nitroalkyls, carboxylalkyls, hydroxylalkyls, sulfoalkyls, etc. Suitable silane compounds include allyl trimethoxy silane, vinyl trimethoxy silane. These compounds can be simply brushed on the surface and dried.

Once primed, a polymer can now be adhered to the modified pyrolytic carbon surface. Polymers particularly suitable for adhering to the modified surface include a natural hydrogel, a synthetic hydrogel, teflon, silicone, polyurethane, polysulfone, cellulose, polyethylene, polypropylene, polyamide, polyimide, polyester, polytetrafluoroethylene, polyvinyl chloride, epoxy, phenolic, neoprene, polyisoprene, and a combination thereof. Additionally, a bio-active compound can be adhered to the modified surface. The bio-active compound can be applied directly to the plasma treated surface, the primed-plasma treated surface, or the primed-plasma treated surface including the polymer adhered thereto. A suitable bio-active compound can be selected from the group consisting of an antithrombotic agent, an antiplatelet agent, an antimitotic agent, an antioxidant, an antimetabolite agent, an anti-inflammatory agent, and a combination thereof. For example, one preferred bio-active compound is heparin. The subsequent addition of a polymer and/or a bio-active compound can be accomplished utilizing conventional techniques known in the art, such as described by Y. Ikada, "Surface Modification of Polymers for Medical Applications," *Biomaterials*, Vol. 15:725–736 (1994); E. A. Kulik, et al., "Peroxide Generation and Decomposition on Polymer Surface," *J. of Polymer Science: Part A: Polymer*

*Chemistry*, Vol. 33:323–330 (1995); and K. Allmθr et al., *J. of Polymer Science*, Vol. 28:173–183 (1990); and M. S. Shue et al., *Contact Angle, Wettability and Adhesion*, pp. 531–545, (ed. K. L Muttal), VSP (1993), for example.

A method in accordance with the present invention is particularly useful to affect sound dampening in a prosthetic heart valve, such as that described in commonly assigned co-pending U.S. Patent Application Ser. No. 09/286,095, wherein silicone rubber can be molded on to the modified pyrolytic carbon surface. It has been found that prosthetic mechanical heart valves are noisy in the sense that the patients can frequently hear the movement of the valve. Further, it has also been found that certain areas of a prosthetic heart valve are particularly susceptible to a high likelihood of thrombus formation and emboli entrapment thus requiring the prescription of anticoagulation therapy to patients.

EXAMPLES

While surface modification methods and apparatuses in accordance with the invention have been described herein, the following non-limiting examples will further illustrate the invention.

The material used in the following Examples were shims of pyrolytic carbon (also referred to herein as PyC) coated on a graphite substrate, the substrate commercially available from Poco Graphite, Inc., A UNOCAL Company, Decatur, Tex., using conventional techniques. All pyrolytic carbon surfaces, whether polished or unpolished, were lapped to achieve a substantially flat surface. The shims were lapped using a lapping machine commercially available under the trade designation PR HOFFMAN PR-1-50-T, from Planetary Lapping & Polishing Machines, Carlisle, Pa. A polished shim is one that has been abraded, as described below, to achieve a smoother surface.

First, an unpolished shim is abraded with an abrasive article including alumina abrasive particles having a size of about 1 micron, the abrasive article commercially available under the trade designation of $AL_2O_3$ MICROGRIT, from Industrial Diamond Products, Houston, Tex., using a centrifugal machine commercially available under the trade designation TIMESAVER HZ8-30 Centrifugal Barrel Finishing Machine, from Timesaver, Minneapolis, Minn. The speed of the centrifugal machine was 160 rpm and was set for a period of time of 90 minutes. Next, this "pre-polished" shim is then abraded with an abrasive article including alumina abrasive particles having a size of about 0.5 microns, the abrasive article commercially available under the trade designation $Al_2O_3$ POLISHING POWDER, from Norton Industrial Ceramics, Inc., Worchester, Mass., using the same centrifugal machine as above. The speed of the centrifugal machine was 160 rpm and was set for a period of time of 90 minutes. All shims were cleaned before they were surface modified or coated. The cleaning procedure was as follows:

The shims were soaked in acetone for 10 minutes. A beaker was filled with a cleaning solution of 30 parts DI water to 1 part cleaning solution commercially available under the trade designation of ULTRAMET, from Buehler, Lake Bluff, Ill. Water was then placed in a conventional ultrasonic cleaner commercially available under the trade designation of ULTRASONIC CLEANER, from Branson Cleaning Equipment Co., Shelton, Conn., to a depth of at least ¼ the height of the beaker. The shims were removed from the acetone and placed in the cleaning solution in the beaker. The beaker containing the shims in the cleaning solution were placed into the ultrasonic cleaner. The ultrasonic cleaner was set for a cleaning time of 3 minutes.

The shims were then removed from the cleaning solution and placed on a drying rack. The shims were rinsed thoroughly with DI water by rinsing 5 times with 2 quarts of DI water at ambient conditions. The shims were next placed into a beaker containing methanol and soaked for 10 minutes at room temperature. The shims were then removed from the methanol and placed on rice paper to dry for at least one half hour at ambient conditions.

All silane coupling agents were applied either directly to PyC surface or to plasma treated PyC surface as follows. The silane coupling agent, commercially available from United Chemical Technologies, Bristol, Pa., was applied to the surface undiluted, unless otherwise noted, with a brush and excess silane was wiped off the surface using a kim wipe. Next, the silane coated surface was put into a convection oven and dried for 5 minutes at 140° F. (60° C.). The dried silane coating can be defined as a primer and the surface can be said to be primed with the silane coupling agent.

All plasma deposition treatments are applied directly to the pyrolytic carbon surface. A description of the plasma reactor was as illustrated in FIG. 1. The pyrolytic carbon shims were placed on the lower electrode. The reaction chamber was evacuated to a base pressure of 0.015 Torr. The operating pressure was set 0.10 Torr and the reaction chamber was allowed to equilibrate for 15 minutes. Mass flow controllers were used to meter the flow of the film forming monomer and argon gas into the reaction chamber, wherein the film forming monomer (e.g., a siloxane monomer) at the rate of 10.0 sccm and the argon was introduced into the reactor at the rate of 0.50 sccm. A glow discharge was created by putting a 100 watt RF power load on the electrodes for 15 seconds exposure time after which the power was turned off, the reactor disassembled, and the plasma coated shims, or leaflet valves, were removed so that they and can be either primed or liquid silicone rubber (abbreviated LSR) coated.

Figure 2A:
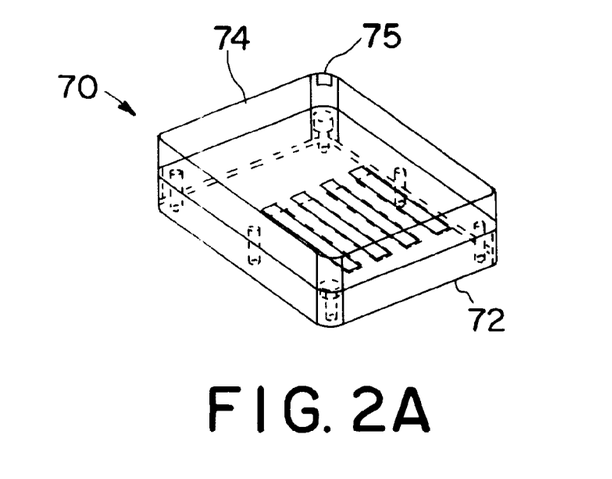
FIG. 2A is a schematic of a mold used in a silicone rubber coating employed in the Examples herein.
Figure 2B:
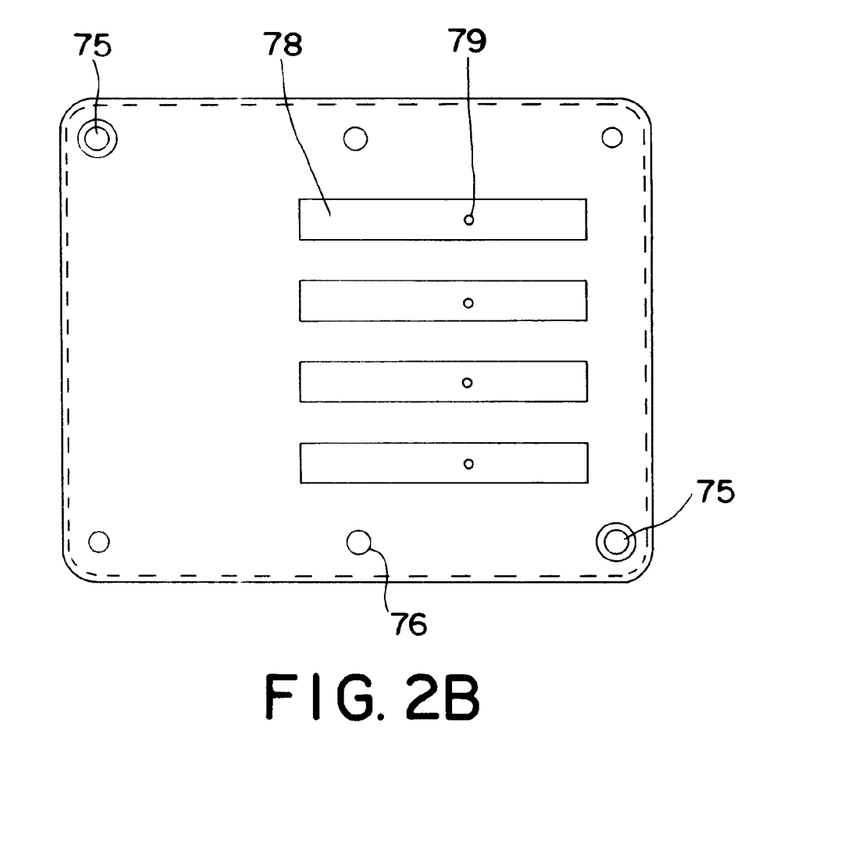
FIG. 2B is a plan view of a bottom portion included in the mold shown in FIG. 2A.

The LSR process and equipment was as follows. An LSR elastomer commercially available under the designation Q7-4850 from Dow Corning was used for coating all shims. As illustrated in FIGS. 2A and 2B, a mold was manufactured which would allow the LSR to coat both sides of a shim that was 1 inch (2.54 cm) in length by 0.234 inch (0.594 cm) in width. FIG. 2A is a schematic of a mold utilized in LSR coating. FIG. 2B is a plan view of a bottom portion included in the mold shown in FIG. 2A. Generally, as shown in FIG. 2A, a mold 70 includes bottom portion 72 and top portion 74 that are securely fastened together via hold-down access 75. Hold-down access 75 is preferably configured to accommodate a screw, nut and bolt, clamp, or any other fastener which will securely fasten bottom portion 72 to top portion 74 during LSR coating to prevent material leakage.

Referring to FIG. 2B, bottom portion 72 includes at least one alignment pin 76 which fits within a corresponding bore in top portion 74 and a bottom portion of hold down access 75. Also included is at least one mold cavity 78 having a length of about 3 inches (7.62 cm), a width of about 0.245 inches (0.622 cm), and a depth of about 0.094 inches (0.24 cm). The shim (or heart valve leaflet) is placed within mold cavity 78 for LSR coating. Each mold cavity 78 includes at least one material inlet 79 for injection of the silicone.

The LSR equipment used was an IPC injection molding machine #71106, from Illinois Precision, Wheaton, Ill. The molding process was a shot size 600 centigrams of LSR, a press pressure of 80 psi, with a cycle time in the mold of 60 sec., a mold temperature of 270° F. (132.2° C.), a speed 1000 and an injection time of 15 sec. Preferably, the LSR injection molding process should be completed within 12 hours of plasma treatment and/or silane primer coating.

Unpolished and polished PyC coated shims were cleaned and LSR coated as described above. These were evaluated for their dry adhesion. These coated shims were evaluated for either their dry adhesion or wet adhesion using a 180° peel test as per ASTM D 903-49.

The unpolished shims had a 180° peel force of 220±108 grams per inch width with failure mode adhesive to the PyC surface. The polished shims had a 180° peel force of 5234±2010 grams per inch width with failure mode cohesive for LSR. The results demonstrated that the polishing process, which oxidizes the carbon surface, improved the adhesion of the LSR to the PyC surface.

Sixteen polished shims were cleaned and LSR coated, these were the control shims. Four of these shims were tested for their dry adhesion, average peel force of 871±370 grams per width inch. Twelve shims were soaked in ringer solution at 70° C. Four of these, soaked for 7 days, had an average peel force of 584±274 grams per inch width, four soaked for 14 days, had an average peel force of 514±348 grams per inch width, four soaked for 28 days, had an average peel force of 291±69 grams per inch width. Mode of failure for the control shims was partial adhesive failure to the PyC surface and partial cohesive LSR failure.

Sixteen polished shims were cleaned, primed with an allyl trimethoxy silane then LSR coated. Four of these shims were tested for their dry adhesion, average peel force of 8113±2119 grams per inch width, failure mode cohesive failure of either the shims or LSR. Twelve of these shims were soaked in ringers solution and tested for their wet adhesion. Four of these soaked for 7 days had an average peel force of 1535±547 grams per inch width, four were soaked for 14 days, had an average peel force of 439±131 grams per inch width, four were soaked for 28 days and an average peel force of 1209±677 grams per inch width. The failure mode for all these shims was adhesive failure to the PyC surface except for two shims which showed partial adhesive and cohesive failure.

Sixteen polished shims were cleaned and treated with a plasma deposition of HMDS (siloxane) treatment then LSR coated. Four of these shims were tested for their dry adhesion, average peel force of 6854±328 grams per inch width. Failure mode was cohesive failure of the LSR coating. Twelve of these shims were soaked in ringers solution and tested for their wet adhesion. Four of these soaked for 7 days had an average peel force of 7648±1418 grams per inch width, with cohesive failure of the LSR, four soaked for 14 days and an average peel force of 6277±763 grams per inch width, with cohesive failure of the LSR except for one shim which showed adhesive failure to the siloxane treatment, four shims soaked for 28 days had an average peel force of 1863±1497 grams per inch width, with a cohesive LSR failure mode except for one shim which showed adhesive failure to the siloxane treatment.

Sixteen polished shims were cleaned, treated with a plasma deposition of HMDS, and primed with a vinyl trimethoxy silane then LSR coated. Four of these shims were tested for their dry adhesion, average peel force of 5280±1106 grams per inch width, failure mode, cohesive failure of the LSR. Twelve shims were soaked in ringer solution and tested for their wet adhesion. Four of these soaked for 7 days had an average peel force of 6423±1936 grams per inch width, failure mode was cohesive failure of LSR, four shim soaked for 14 days had an average peel force of 7184±4590 grams per inch width, failure mode was cohesive failure of LSR, four shims soaked 28 days and had an average peel force of 8473±3662 grams per inch width, failure mode was cohesive failure of either the PyC shims or the LSR coating.

The data discussed above is summarized in Table 1 below.

TABLE 1

| Shim treatment | Average Peel Force (in grams) | | | |
| --- | --- | --- | --- | --- |
| | Dry Adhesion | 7 days | 14 days | 28 days |
| Control (LSR coated) | 871 ± 370 | 584 ± 274 | 514 ± 348 | 291 ± 69 |
| primed/LSR coated | 8113 ± 2119 | 1535 ± 547 | 439 ± 131 | 1209 ± 677 |
| plasma/LSR coated | 6854 ± 328 | 7648 ± 1418 | 6277 ± 763 | 1863 ± 1497 |
| plasma/primed/LSR coated | 5280 ± 1106 | 6423 ± 1936 | 7184 ± 4590 | 8473 ± 3662 |

The adhesion data shows a general wet adhesion relationship, from greatest to lowest, of siloxane treatment/silane primer>siloxane treatment>silane primer>polished surface (oxidation)>upolished surface. The adhesion data demonstrated that modified pyrolytic carbon surface and silicone rubber has a wet adhesion peel force of at least 10 times greater than the wet adhesion peel force between an unmodified pyrolytic carbon and silicone rubber as measured by ASTM D 903-49 after 28 days in an aqueous environment. Although the standard deviations appeared to be relatively high, it is believed that these deviations were a result in the type of failure observed for each of the shim tested. For example, in a group of shims, the failure may be due to cohesive failure, adhesive failure, and a combination of both. Depending upon the type of failure, the result of each shim can vary from the others but are averaged together, as indicated in the table above.

The effects of the present invention were also evaluated in a simulated bio-environment to test the physical stress of the material. In this evaluation, eight pyrolytic carbon samples in a configuration of a heart valve leaflet were treated with a plasma deposition of HMDS, and primed with a vinyl trimethoxy silane then LSR coated.

Figure 3:
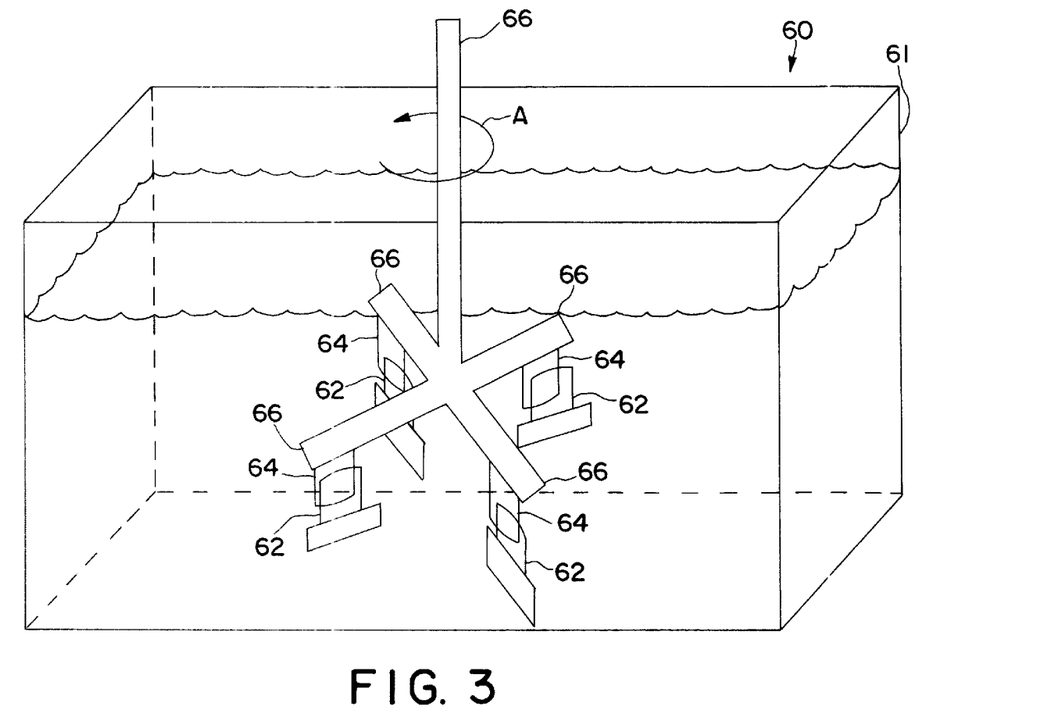
FIG. 3 is a schematic of a dynamic test utilized to evaluate a surface modified in accordance with the present invention in a simulated bio-environment, as described in the Examples.

An apparatus 60 used in the evaluation is depicted in FIG. 3. Four of the treated samples were stationary samples 62, wherein each stationary sample 62 was fixed at 90 degrees relative to the bottom of a test tank 61. The four remaining samples were moving samples 64, wherein each moving sample 64 was mounted on a spoke 66 projecting from a center shaft 65. Each of the four samples 64 were mounted such that each spoke 66 was rotated by the center shaft 65, each moving sample 64 would contact each stationary sample 62. As a moving sample 64 contacted the stationary sample 62, a surface of the moving sample 62 would contact and move across a surface of the stationary sample 62. In this manner, a simulated "wear" test was provided due to the repeated surface contact of the samples.

The test was conducted in Ringer's solution (162.76 gm of NaCl, 5,18 gm of KCl, 6.25 gm of 111 formula weight of $CaCl_2$ in 5 gallons (18.93 liters) of deionized water) at 37° C. The shaft was rotated at a speed of 300 RPM, indicated as Arrow "A." In each revolution of the shaft, each moving sample 64 would contact the four stationary samples 62 one time, resulting in an actual cyclic rate per sample of 1200 RPM.

The test was stopped at 40 million RPM and the samples were taken out of the test tank 61 for evaluation. For each sample, a maximum wear depth was examined. After the samples were examined, they were repositioned in the test tank and the test resumed.

After 80 million RPM, no polymer delamination of the plasma coating from the PyC substrate was detected. Although wear burnishing on the coating could be seen, the maximum wear depth was so insignificant so as to be unmeasureable.

| List of Components for Figures | |
|---|---|
| 10 | plasma reactor |
| 12 | reaction chamber |
| 14 | power source |
| 16 | upper electrode |
| 18 | lower electrode |
| 20 | vacuum pump |
| 22 | reactant monomer source |
| 24 | at least one pyrolytic carbon surface |
| 34 | throttle valve |
| 38 | inert gas source |
| 40 | plasma |
| 60 | evaluation apparatus |
| 61 | test tank |
| 62 | stationary sample(s) |
| 64 | moving sample(s) |
| 65 | shaft |
| 66 | spoke |
| 70 | liquid silicone rubber mold |
| 72 | bottom portion of the mold |
| 74 | top portion of the mold |
| 75 | hold-down access |
| 76 | alignment pin |
| 78 | mold cavity |
| 79 | material (silicone) inlet |

The complete disclosures of all patents, patent applications, and publications are incorporated herein by reference as if individually incorporated. The above disclosure is intended to be illustrative and not exhaustive. The description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached thereto.

What is claimed is:

1. A method for modifying a pyrolytic carbon surface comprising:
   providing a substrate having at least one pyrolytic carbon surface to a reaction chamber,
   depositing an oxygen-containing, silicon-containing film forming monomer on the at least one pyrolytic carbon surface, wherein the oxygen-containing, silicon-containing film; forming monomer is a siloxane; and
   priming the at least one pyrolytic carbon surface having the oxygen-containing, silicon-containing film forming monomer deposited thereon with a silane compound.

2. The method of claim 1 further comprising adding a polymer to the at least one pyrolytic carbon surface primed with the silane compound.

3. The method of claim 2 wherein the polymer is selected from the group consisting of a natural hydrogel, a synthetic hydrogel, silicone, polyurethane, polysulfone, cellulose, polyethylene, polypropylene, polyamide, polyimide, polyester, polytetrafluoroethylene, polyvinyl chloride, epoxy, phenolic, neoprene, polyisoprene, and a combination thereof.

4. The method of claim 1 further comprising adding a bio-active compound to the at least one pyrolytic carbon surface primed with the silane compound.

5. The method of claim 4 wherein the bio-active compound is selected from the group consisting of an antithrombotic agent, an antiplatelet agent, an antimitotic agent, an antioxidant, an antimetabolite agent, an anti-inflammatory agent, and a combination thereof.

6. The method of claim 1 wherein depositing the oxygen-containing, silicon-containing film forming monomer on the at least one pyrolytic carbon surface comprises plasma depositing the film forming monomer in the presence of a gas selected from the group consisting of argon, helium, nitrogen, neon, and a combination thereof.

7. The method of claim 6 wherein the film forming monomer is in a ratio with the gas of about 20 parts film forming monomer to about 1 part gas.

8. The method of claim 1 wherein plasma depositing the film forming monomer occurs for a time period from about 10 minutes or less.

9. A method for increasing adhesion between a pyrolytic carbon surface and a polymer comprising:
   providing a substrate having, at least one pyrolytic carbon surface to a reaction chamber;
   depositing an oxygen-containing, silicon-containing film forming monomer on the at least one pyrolytic carbon surface, wherein the oxygen-containing, silicon-containing film forming monomer is a siloxane;
   priming the at least one pyrolytic carbon surface having the oxygen-containing, silicon-containing film forming monomer deposited thereon with a silane compound; and
   adding the polymer to the at least one pyrolytic carbon surface primed with the silane compound.

10. The method of claim 9 wherein the polymer is selected from the group consisting of a natural hydrogel, a synthetic hydrogel, silicone, polyurethane, polysulfone, cellulose, polyethylene, polypropylene, polyamide, polyimide, polyester, polytetrafluoroethylene, polyvinyl chloride, epoxy, phenolic, neoprene, polyisoprene, and a combination thereof.

11. The method of claim 9 further comprising applying a bio-active compound to the polymer, wherein the bio-active compound is selected from the group consisting of an antithrombotic agent, an antiplatelet agent, an antimitotic agent, an antioxidant, an antimetabolite agent, an anti-inflammatory agent, and a combination thereof.

12. The method of claim 9 wherein deposing an oxygen-containing, silicon-containing film forming monomer on the at least one pyrolytic carbon surface comprises plasma depositing the film forming monomer in the presence of a gas selected from the group consisting of argon, helium, nitrogen, neon, and a combination thereof.

13. A method for attaching a polymer to a prosthetic heart valve comprising at least one pyrolytic carbon surface comprising:
   forming a film on the at least one pyrolytic carbon surface of the heart valve, wherein the film is formed from an oxygen-containing, silicon-containing film forming monomer, and further wherein the oxygen-containing, silicon-containing film forming monomer is a siloxane;
   priming the at least one pyrolytic carbon surface having the oxygen-containing, silicon-containing film forming monomer film thereon with a silane compound; and
   adding the polymer to the at least one pyrolytic carbon surface primed with the silane compound.

14. The method of claim 13 wherein the polymer is selected from the group consisting of a natural hydrogel, a synthetic hydrogel, silicone, polyurethane, polysulfone, cellulose, polyethylene, polypropylene, polyamide, polyimide, polyester, polytetrafluoroethylene, polyvinyl chloride, epoxy, phenolic, neoprene, polyisoprene, and a combination thereof.

15. The method of claim 13 further comprising adding a bio-active compound to the at least one pyrolytic carbon surface primed with the silane compound prior to adding the polymer to the at least one pyrolytic carbon surface primed with the silane compound.

16. The method of claim 15 wherein the bio-active compound is selected from the group consisting of an antithrombotic agent, an antiplatelet agent, an antimitotic agent, an antioxidant, an antimetabolite agent, an anti-inflammatory agent, and a combination thereof.

17. The method of claim 13 further comprising adding a bio-active compound to the at least one pyrolytic carbon surface prior to priming the at least one pyrolytic carbon surface having the oxygen-containing, silicon-containing film forming monomer film thereon with a silane compound.

18. The method of claim 13 further comprising adding a bio-active compound to the at least one pyrolytic carbon surface after adding the polymer to the at least one pyrolytic carbon surface primed with the silane compound.

19. The method of claim 13 wherein forming the film comprises plasma depositing the siloxane on the at least one pyrolytic carbon surface.

20. The method of claim 19 wherein plasma depositing the film forming monomer occurs for a time period from about 10 minutes or less.

21. The method of claim 19, wherein plasma depositing the film forming monomer comprises depositing the film forming monomer in the presence of a gas selected from the group consisting of argon, helium, nitrogen, neon, and a combination thereof.

22. The method of claim 21 wherein the film forming monomer is in a ratio with the gas of about 20 parts film forming monomer to about 1 part gas.

* * * * *